United States Patent [19]

Wulff et al.

[11] Patent Number: 5,959,160
[45] Date of Patent: Sep. 28, 1999

[54] PURIFICATION OF P,P-BISPHENOLATE SOLUTIONS

[75] Inventors: Claus Wulff, Krefeld; Kurt-Peter Meurer, Leverkusen, both of Germany; Tony van Osselaer, Belsele; Roelof Boyens, Deurne, both of Belgium; Jürgen Hinz, Krefeld, Germany

[73] Assignee: Bayer AG, Leverkusen, Germany

[21] Appl. No.: 08/819,418

[22] Filed: Mar. 17, 1997

[30] Foreign Application Priority Data

Mar. 21, 1996 [DE] Germany .................... 196 11 141

[51] Int. Cl.$^6$ ...................................... C07C 37/68
[52] U.S. Cl. ............................................... 568/724
[58] Field of Search .................... 568/747, 723, 568/724; 562/491

[56] References Cited

U.S. PATENT DOCUMENTS 4,400,553  8/1983  Aneja .

FOREIGN PATENT DOCUMENTS 758 636    8/1996   European Pat. Off. .
44 13 396  10/1995  Germany .
92 00943   1/1992   WIPO .

OTHER PUBLICATIONS

Chemical Abstracts, vol. 119, No. 26, Dec. 27, 1993, Abstract No. 271942g.

*Primary Examiner*—Michael L. Shippen
*Attorney, Agent, or Firm*—Connolly, Bove, Lodge & Hutz LLP

[57] ABSTRACT

The invention relates to a process for the purification of p,p-bisphenolate solutions such as are obtained in the production of bisphenolates from soda lye and bisphenols by extraction.

4 Claims, No Drawings

PURIFICATION OF P,P-BISPHENOLATE SOLUTIONS

The invention relates to a process for the purification of p,p-bisphenolate solutions such as are obtained in the production of bisphenolates from soda lye and bisphenols by extraction.

The production of high-purity sodium p,p-bisphenolate solutions (NaBPA) is known. By multiple re-crystallization of the bisphenol-A or by distillation of the bisphenol A melt it is possible to produce high-purity bisphenol-A and then to produce high-purity sodium bisphenolate solutions continuously by converting equivalent quantities of bisphenol-A with soda lye (e.g. DE-A 4 413 396).

It has now been found that p,p-bisphenolate solutions can be extracted with halogen-free organic solvents in such a way that the extracted p,p-bisphenolate solution contains less than 0.1 wt. % of isomer of the corresponding bisphenol.

The invention relates to a process for the purification of 14 to 18 wt. % phenolic p,p-bisphenolate solutions which are obtained in the production of p,p-bisphenols, characterized in that in the p,p-bisphenolate solution with a content of at least 99.5 wt. % of p,p-bisphenolate the isomers of the bisphenol are extracted by extractive removal with a halogen-free organic solvent and the p,p-bisphenolate content is brought to >99.95 wt. %, related to dissolved solid.

The phenolic p,p-bisphenolate solutions to be purified according to the invention contain the known by-products which also arise in the production of bisphenol-A from phenol and acetone, such as isomers of bisphenol-A, indanes and alkylphenolates. This p,p-bisphenolate solution is obtained by adding alkali (e.g. NaOH) to the converted reaction solution obtained in the bisphenol-A production.

The p,p-bisphenolate solution to be purified by extraction according to the invention has a concentration of 14 to 18 wt. % of p,p-bisphenolate, preferably 14.5 wt. %. Preferably the p,p-bisphenolate is present as Na salt (NaBPA).

The extraction can be carried out continuously or discontinuously, preferably continuously, e.g. in mixer-settler apparatus.

Halogen-free organic solvents are used as extractants, such as ketones (e.g. methylisobutylketone) and esters such as ethyl acetate, preferably ethyl acetate.

The extractant can be separated from the extract, by distillation for example, and reused. An extract residue obtained in this way contains the high-boiling isomers which arise when phenol is converted with acetone to bisphenol-A. These isomers (isomer residue) can be isomerized on ion exchangers for example or be eliminated from the process together with residual resins of bisphenol-A production.

EXAMPLES

Example 1

A 14.5% NaBPA solution with a p,p-BPA content of 99.51 wt. % was produced. 66 ppm of phenol, 89 ppm of 4-tert.-butylphenyl, 2160 ppm of o,p-BPA, 99 ppm of p,p-methylBPA, 39 ppm of indanes, 223 ppm of trisphenol and 1790 ppm of Mol 402 were also present in the alkaline solution.

One unit of volume of a 14.5 % sodium bisphenolate solution produced in this way, with an OH⁻ excess of 0.20% was extracted four times with the equivalent unit of volume of ethyl acetate for 1 minute. The phases were separated, the BPA content in the aqueous and in the organic phase determined by GC chromatography.

A BPA purity of 99.96 wt. % of p,p-BPA was determined in the aqueous phase by GC chromatography. The Mol 402 content was 20 ppm, the trisphenol content 108 ppm, the indanes content <20 ppm, the p,p-methylBPA content <30 ppm, the o,p-BPA content 11 ppm, the 4-tert.-butylphenol content <10 ppm and the phenol content 54 ppm.

Example 2

As in Example 1, but with the difference that methylisobutylketone was used instead of ethyl acetate.

A BPA purity of 99.89 wt. % of p,p-BPA, 54 ppm of phenol, <10 ppm of 4-tert.-butylphenol, 508 ppm of o,p-BPA, 80 ppm of p,p-methylBPA, 27 ppm of indanes, 180 ppm of trisphenol and 108 ppm of Mol 402 were found in the aqueous phase.

Comparative Example A

As in Example 1 but with the difference that chlorobenzene was used as the solvent.

It was not possible to extract any isomers (detection limit).

Comparative Example B

As in Example 1 but with the difference that chlorobenzene/dichloromethane (50/50) was used as the solvent.

It was not possible to extract any isomers (detection limit).

We claim:

1. A process for purifying a solution of p,p-bisphenolate in phenol, which solution contains 14–18 weight percent p,p-bisphenolate, the p,p-bisphenolate in the solution being at least 99.5 weight percent pure p,p-bisphenolate, which comprises extracting the solution with a halogen-free solvent to bring the pure p,p-bisphenolate content to greater than 99.95 weight percent.

2. The process of claim 1, wherein the p,p-bisphenolate solution is obtained from the production of p,p-bisphenols.

3. The process of claim 1, wherein the halogen free solvent is a ketone or an ester.

4. The process of claim 1, wherein the halogen free solvent is ethyl acetate.

* * * * *